United States Patent [19]

Oh

[11] Patent Number: 5,250,258
[45] Date of Patent: Oct. 5, 1993

[54] METHOD FOR PURIFYING AND ACTIVATING AIR AND APPARATUS THEREFOR

[76] Inventor: Byeung-ok Oh, 10-9 Haewha-Dong, Jongro-Gu, Seoul, Rep. of Korea

[21] Appl. No.: 833,705

[22] Filed: Feb. 11, 1992

[51] Int. Cl.⁵ .............................................. A61L 9/18
[52] U.S. Cl. ...................................... 422/22; 422/120; 422/121; 356/436; 356/437; 356/438; 356/374; 250/504 R; 250/428; 250/432 R
[58] Field of Search ......................... 422/22, 120, 121; 250/454.11, 455.11, 428, 432 R, 495.1, 504 R; 356/432, 437, 438, 440, 246, 374, 436

[56] References Cited

U.S. PATENT DOCUMENTS

| | | | |
|---|---|---|---|
| 3,696,247 | 10/1972 | McIntosh et al. | 356/323 |
| 3,920,336 | 11/1975 | Sackett | 356/440 |
| 4,050,823 | 9/1977 | Frankenberger | 356/437 |
| 4,366,525 | 12/1982 | Baumgartner | 422/121 |
| 4,376,642 | 3/1983 | Verity | 422/121 |
| 4,857,895 | 8/1989 | Kaprelian | 356/438 |
| 5,116,120 | 5/1992 | Picker | 356/246 |

Primary Examiner—James C. Housel
Assistant Examiner—Stephanie Smith
Attorney, Agent, or Firm—Lowe, Price, LeBlanc & Becker

[57] ABSTRACT

An air treatment apparatus includes a chamber designed to provide infrared radiation at a predetermined wavelength. Atmospheric air is passed through the chamber such that carbon dioxide molecules in the chamber achieve a higher energy state. Atmospheric air containing the higher energy state carbon dioxide molecules is discharged from the apparatus into the atmosphere. The atmospheric air containing higher energy or activated carbon dioxide may be used in a given space to overcome lethargic conditions produced by prior art air treatment devices such as air conditioners. The atmospheric air may be filtered prior to entering and after discharging from the treatment chamber for further air treatment. Heat may also be provided in the chamber to oxidize impurities in the air for further purification and air treatment. A method is provided whereby atmospheric air passes through the infrared radiating chamber to activate carbon dioxide molecules therein. The method produces atmospheric air containing carbon dioxide molecules in a higher energy state, the increased energy in the carbon dioxide molecules available to humans to overcome lethargic conditions produced by other prior art air purifying devices.

16 Claims, 8 Drawing Sheets

METHOD FOR PURIFYING AND ACTIVATING AIR AND APPARATUS THEREFOR

FIELD OF THE INVENTION

The present invention is directed to a method for purifying and activating air and an apparatus therefor. More particularly, the method and apparatus purify air by thermally decomposing impurities therein. In another aspect of the invention, air containing carbon dioxide is subjected to infrared radiation to increase the energy state of carbon dioxide molecules in the air for absorption by the human body.

BACKGROUND OF THE INVENTION

In the prior art, various types and shapes of air purifiers have been proposed. One example of a prior art system used for purifying air includes the combination of a multi-step filter and an electrostatic precipitator to remove impurities in a stream of air. These prior art systems may also include an air conditioning aspect which further cools the purified air. Another prior art system includes air ionizing systems which remove impurities in the air using electrostatic precipitation.

However, prior art systems utilizing air conditioners contain drawbacks when in operation over long periods of time. One disadvantage associated with the air conditioners is that the human body may become lethargic after being subjected to air conditioning for a long period of time. In view of the disadvantages of known prior art air purifying devices, a need has developed to provide improved air treating devices which overcome lethargic conditions created by prior art devices.

In response to this need, the present invention provides a method and apparatus for purifying and activating air to overcome lethargic conditions caused by prior art air purifying and conditioning systems.

SUMMARY OF THE INVENTION

It is accordingly a first object of the present invention to provide a method for purifying and activating air and an apparatus therefor.

It is a further object of the present invention to provide a method and apparatus which thermally decomposes impurities in the air to provide a purified stream of air for inhalation by living beings.

It is a yet further object of the present invention to provide a method and apparatus which subjects carbon dioxide molecules in air to infrared radiation such that the carbon dioxide molecules achieve a higher energy state, the increased energy in the carbon dioxide molecules capable of being absorbed by living beings, in particular, humans. Other objects and advantages of the present invention will become apparent as the description proceeds.

In satisfaction of the foregoing objects and advantages, there is provided an apparatus for activating air comprising a chamber having an inlet and outlet and wherein the chamber is configured in a Rowland circle shape. Within the chamber is an infrared radiation source for emitting infrared radiation at a given wavelength. Also included in the chamber is a diffraction grating which is designed to receive the infrared radiation emitted from the infrared radiation source and correct it to a wavelength range between 2300–2400 cm$^{-1}$. A fan is provided to move atmospheric air through the chamber while being subjected to the infrared radiation. A filter may be provided at the inlet to the fan and outlet from the chamber to assist in purifying air passing through the apparatus.

By subjecting the atmospheric air to the infrared radiation at a predetermined wavelength, carbon dioxide molecules therein are activated to a higher energy level. As will be described in more detail hereinafter, activation of air refers to the molecules of carbon dioxide absorbing infrared radiation to achieve a higher energy level.

The apparatus of the present invention may also include a heating device disposed within the chamber to thermally decompose or oxidize any impurities in the atmospheric air passing therethrough.

The present invention also provides for a method of treating air comprising steps of obtaining a continuous source of air having carbon dioxide and impurities therein, providing a source of infrared radiation having a wavelength between about 2300–2400 cm$^{-1}$ and subjecting the impurity and carbon dioxide laden air to the infrared radiation such that the carbon dioxide achieves a higher energy state. The treated air is then returned to the atmosphere. The inventive method may also include the step of filtering the air before and after the infrared radiating step. Moreover, impurities in the atmospheric air may be subjected to heating to thermally decompose any impurities therein to further purify the air.

BRIEF DESCRIPTION OF THE DRAWINGS

Reference is now made to the Drawings accompanying the application wherein.

DESCRIPTION OF THE PREFERRED EMBODIMENT

The present invention is directed to an apparatus and method for treating air and activating carbon dioxide molecules therein.

In the atmosphere, the concentration of carbon dioxide is typically 300–5000 ppm. The carbon dioxide gas is a linear molecule of three atoms with 4 degrees of free vibrations. Two bent vibrations overlap and another vibrational direction is evident in the spectrum of carbon dioxide gas. At this point, the carbon dioxide molecule is in the shape of a fan. The distance between the carbon and oxygen atoms is 1.15 Å and the $\pi$-bond is perpendicular. When carbon dioxide gas absorbs infrared radiation, the dipole moment changes and the energy state of the carbon dioxide gas molecule is increased. This increased energy state occurs at a peak frequency of about 2300-2400 cm$^{-1}$. The term activated through the application is used to define this increased energy state.

A similar situation occurs during sunrise. As the sun rises in the eastern sky, being colored over by red hues, the solar radiation includes an infrared radiation portion. As a result of the angle of the infrared radiation during sunrise, peak frequencies in the range of 2300-2400 cm$^{-1}$ are present. This infrared radiation may then be absorbed by carbon dioxide gas molecules in the atmosphere to produce activation thereof. After sunrise, and due to the changing position of the sun, the peak frequencies necessary to activate the carbon dioxide molecules in the atmosphere are no longer present.

However, due to the limited time span during sunrise, the availability of activated carbon dioxide gas and use of the increased energy state thereof is limited. As stated above, carbon dioxide concentration typically is about 300 ppm. In below ground environments such as mining or subway tunnels, carbon dioxide levels are higher, for example as high as 8-11%. Although these levels of carbon dioxide provide higher levels of energy when activated, prolonged exposure to these levels of carbon dioxide is not recommended since oxygen is deficient.

As part of the present invention, it has also been discovered that carbon dioxide molecules may achieve the activated and higher energy state during the process of smoking cigarettes. Smoke from a cigarette was collected by a hand sampler which absorbed 1.0 liters/minute of cigarette smoke. The smoke prior to absorption passed through a multi-core filter having a micro-diameter of 0.3 microns. The multi-core filter eliminated other harmful impurities in the smoke. It should be understood that the smoke collected was a result of the cigarette smoking process and not smoke after respiration by a human.

Figure 1:
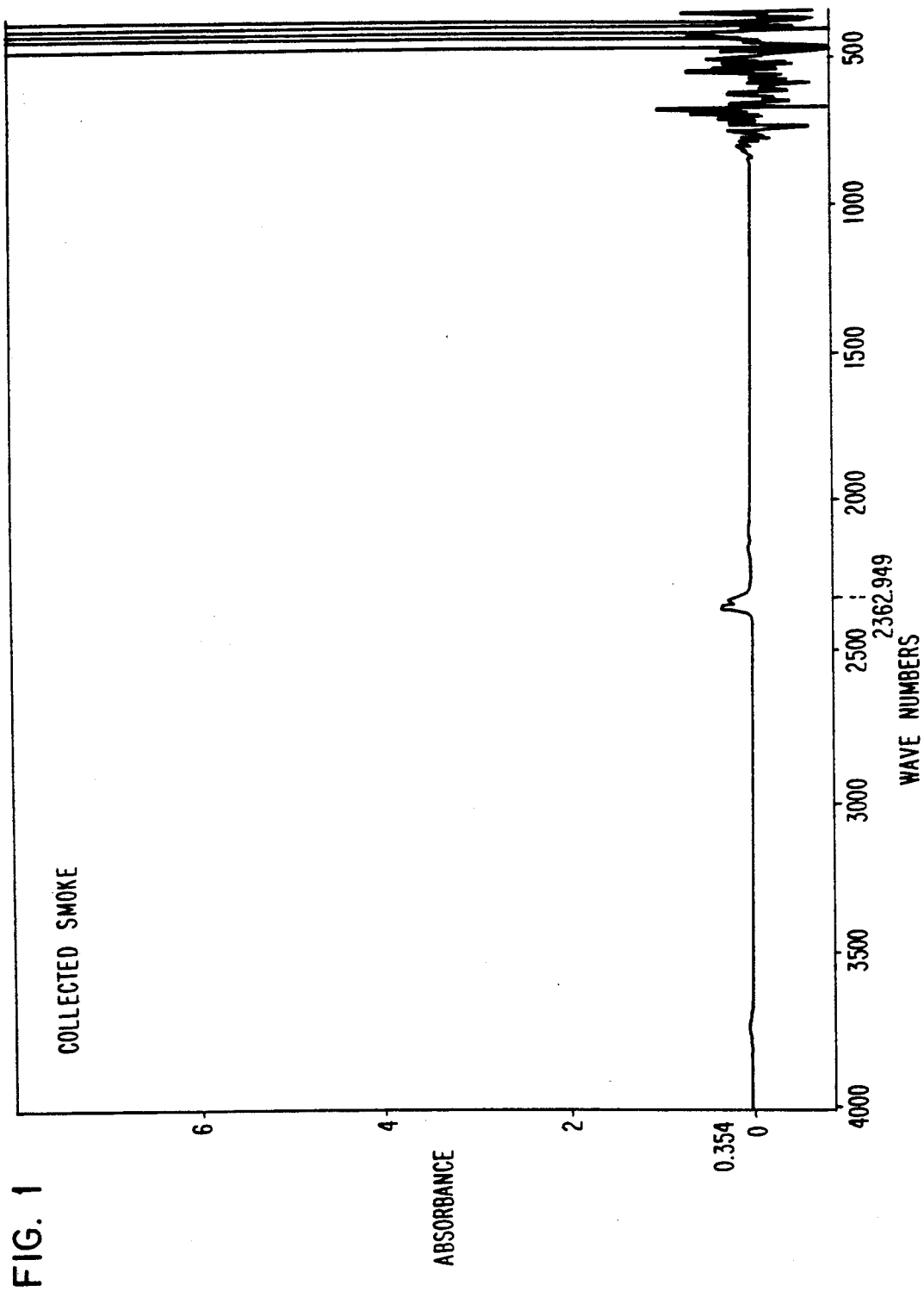
FIG. 1 is a graph showing the spectrum of smoke collected from a cigarette.

With reference now to FIG. 1, a spectrum using known infrared spectrophotometry equipment was obtained for the collected smoke. The collected smoke contained approximately 0.5% carbon dioxide gas. As can be seen from FIG. 1, the peak on the spectrum occurred at 2362.949 cm$^{-1}$ and showed an absorbance of 0.354. The spectrum shown in FIG. 1, shows that activated carbon dioxide is generated during the smoking process.

Figure 2:
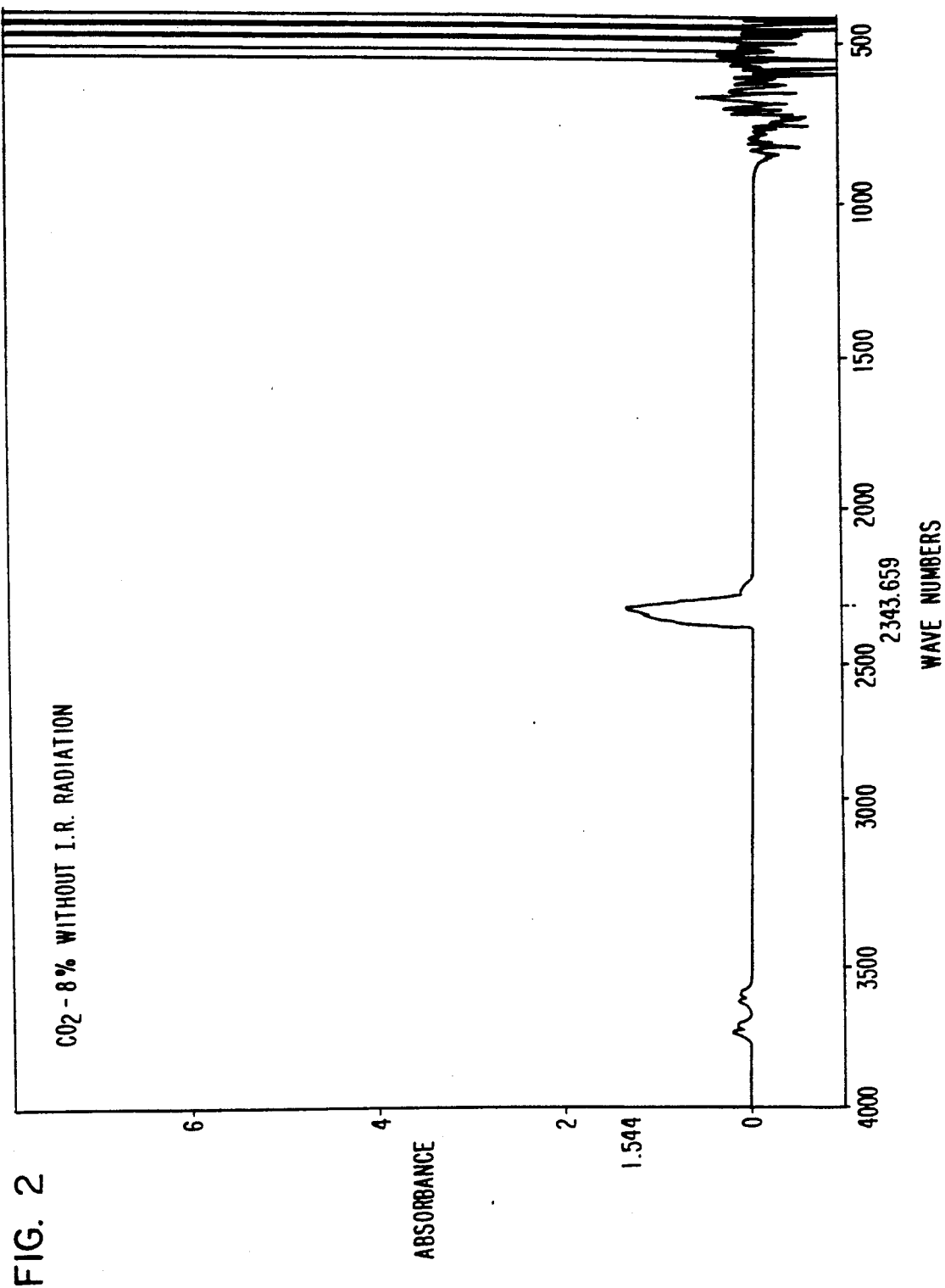
FIG. 2 is a graph showing the spectrum of air having eight percent $CO_2$ without exposure to infrared radiation.
Figure 3:
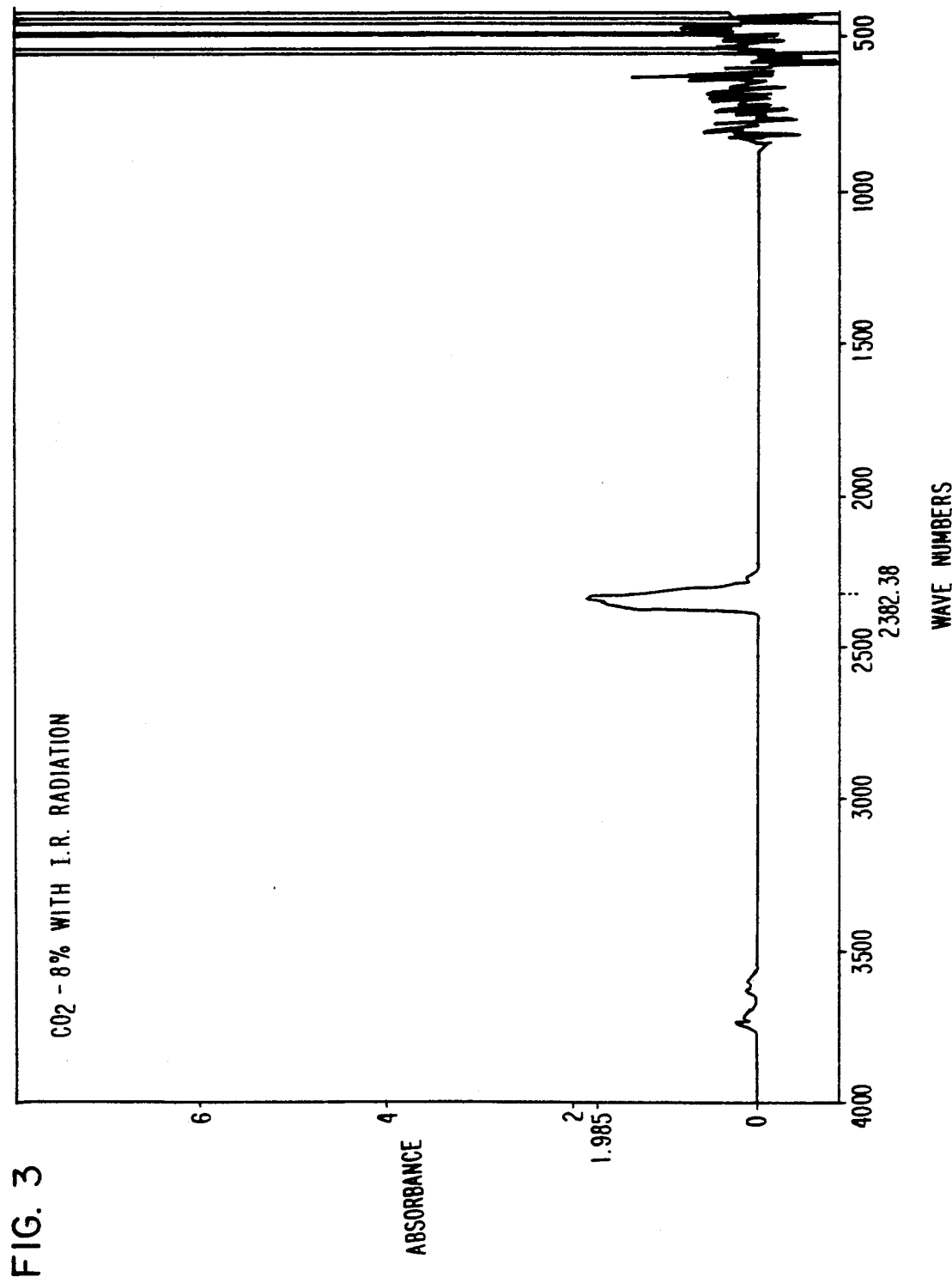
FIG. 3 is a graph showing the spectrum of air having eight percent $CO_2$ after being subjected to infrared radiation according to the present invention.

With reference to FIGS. 2 and 3, a comparison is made between eight percent levels of carbon dioxide in atmosphere being subjected to infrared radiation according to the present invention. FIG. 2 shows a line spectrum of atmosphere containing 8% CO$_2$ without being subjected to infrared radiations depicting a peak at frequency 2343.659 and an absorbance value of 1.544. When subjecting the carbon dioxide at an eight percent level to infrared radiation according to the present invention, the absorbance value increases to 1.985, see FIG. 3. The difference in absorbances between FIGS. 2 and 3 is 0.441. This indicates that the carbon dioxide at eight percent level being subjected to infrared radiation according to the present invention achieves an activated or increased energy state. Although the eight percent carbon dioxide levels indicate that a high energy state can be achieved by subjecting the gas to infrared radiation, these levels of carbon dioxide, as described above, are harmful.

Figure 4:
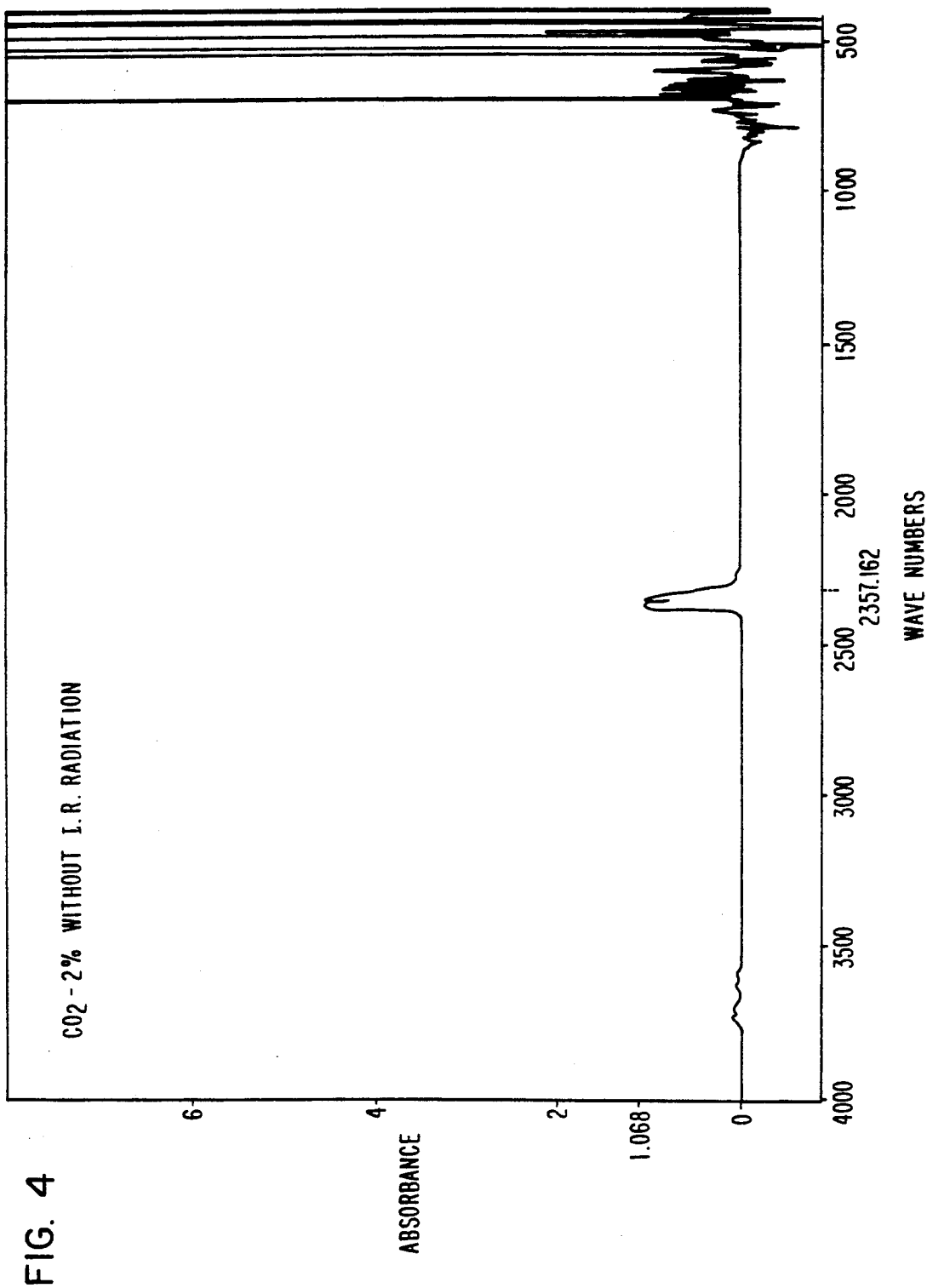
FIG. 4 is a graph showing the spectrum of gas exhaled from a human body having two percent $CO_2$ without being subjected to infrared radiation according to the present invention.
Figure 5:
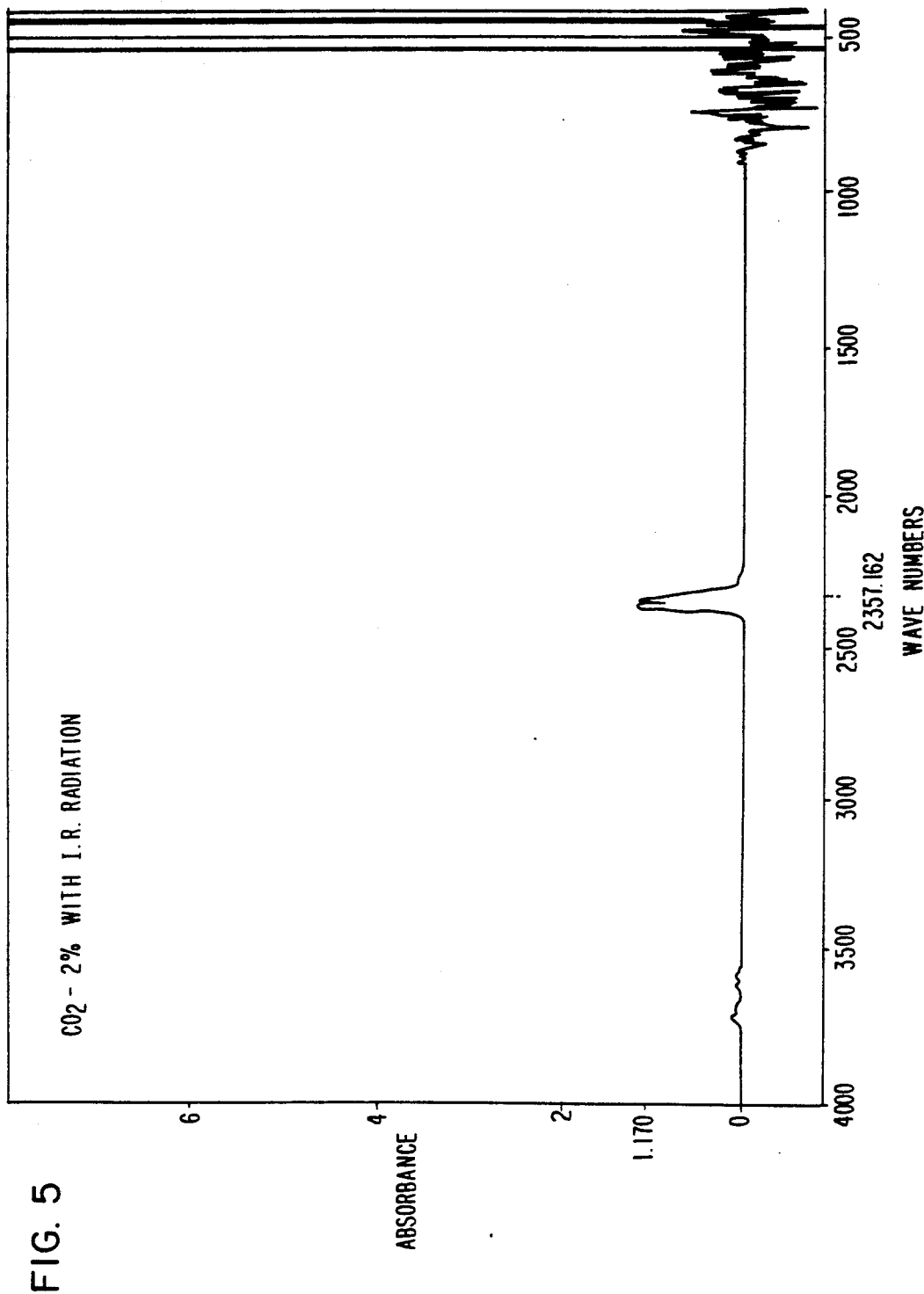
FIG. 5 is a graph showing the spectrum under conditions described for FIG. 4 but with application of infrared energy.

In another experiment, and with reference to FIGS. 4 and 5, the effect of infrared radiation on gas respirated from a human body is shown. Subjecting the gaseous respiration to infrared radiation shows an absorbance level of 1.170 see FIG. 5. In contrast, FIG. 4 shows that the absorbance level of the two percent carbon dioxide containing respirated gas without infrared radiation is 1.068. The difference between the two absorbance values in FIGS. 4 and 5 is 0.102 which reflects how much energy a human body can absorb at natural conditions, i.e. an amount of energy equivalent to the difference in absorption value, 0.102.

Figure 6:
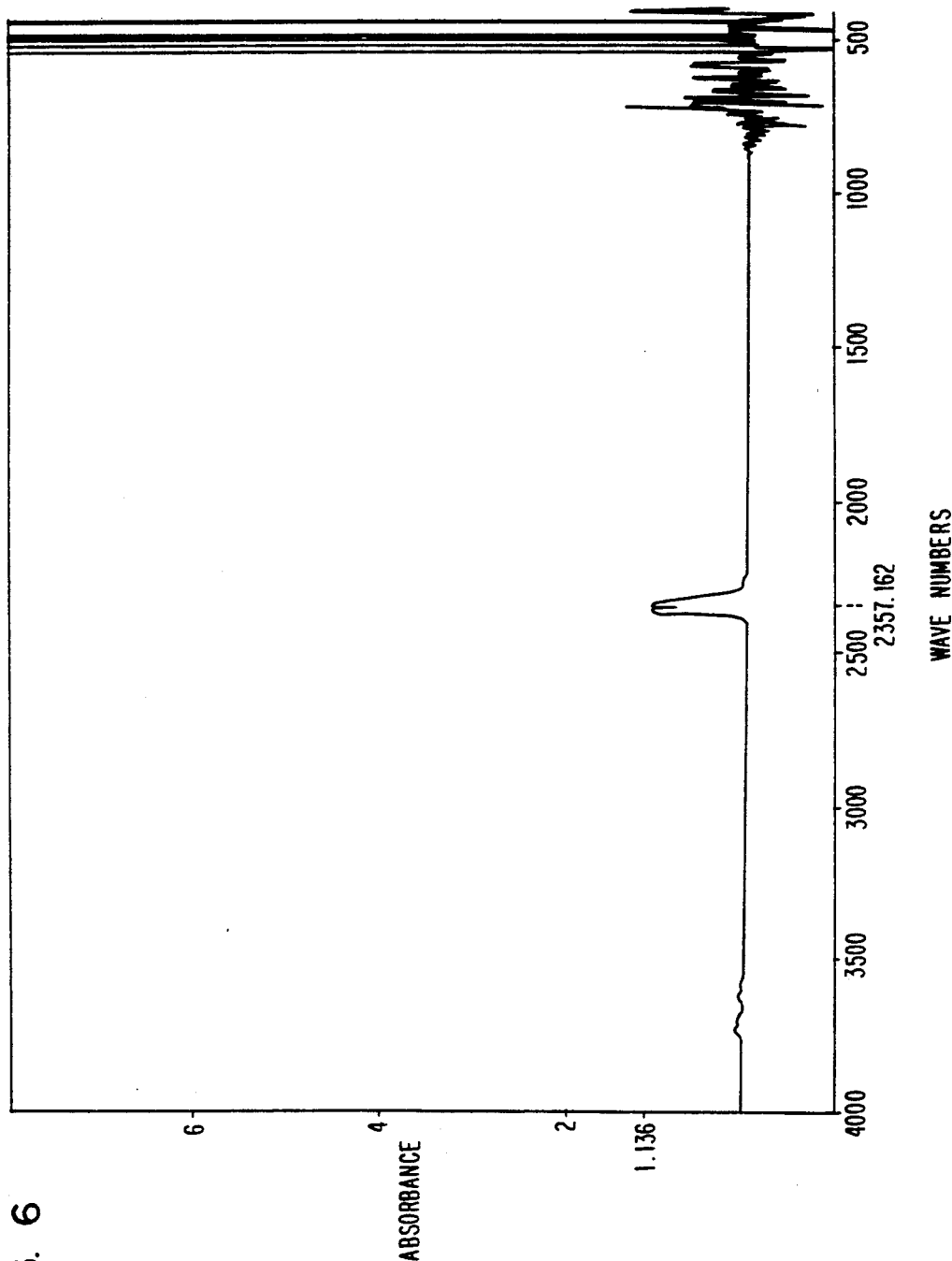
FIG. 6 is a graph showing the spectrum of gas exhaled from a human body after inhaling smoke from a lighted cigarette.

FIG. 6 depicts the spectrum of the respiration of a human body after inhaling smoke from a burning cigarette. Therein, an absorbance level of 1.136 is shown having a peak frequency of 2357.162.

The Table listed below shows the frequency and absorbance level for FIGS. 1-6.

TABLE

| Name | Frequency | Absorbance |
| --- | --- | --- |
| FIG. 1 - Cigarette smoke | 2362.949 | 0.354 |
| FIG. 2 - CO$_2$ 8% | 2343.659 | 1.544 |
| FIG. 3 - CO$_2$ 8% | 2382.238 | 1.985 |
| FIG. 4 - CO$_2$ 2% | 2357.162 | 1.068 |
| FIG. 5 - CO$_2$ 2% | 2357.162 | 1.170 |
| FIG. 6 - After smoking | 2357.162 | 1.136 |

Using the values from these figures, an estimate of the amount of energy absorbed by a human body may be made during the smoking process. FIG. 4 shows that the absorbance level of a person's respiration in a natural state is 1.068. During smoking, activated carbon dioxide is introduced into a human body having an absorbance level of 0.354. The level of absorbance after smoking is shown in FIG. 6 as 1.136. By adding the energy associated with the smoke from a cigarette, i.e. 0.354, to the energy level depicted in FIG. 4, i.e. 1.068, gives a value of energy absorbance prior to exhalation. By subtracting the value of absorbance upon exhalation, i.e. FIG. 6—1.136, an overall energy absorption of 0.286 is achieved. The following equation more clearly shows the calculation to determine the amount of energy absorbed during smoking:

FIG. 5 + FIG. 1 − FIG. 6 = energy absorbed
(1.068 + 0.354) − 1.136 = 0.286

By this calculation, it is shown that the process of cigarette smoking results in absorbance of energy by the human body.

However, it is well known that smoking of cigarettes produces harmful effects in spite of the energy absorbance due to the activation of carbon dioxide molecules in the smoke. The present invention provides a means and method for absorbance of the energy in activated carbon dioxide without the harmful effects associated with cigarette smoking.

Figure 7:
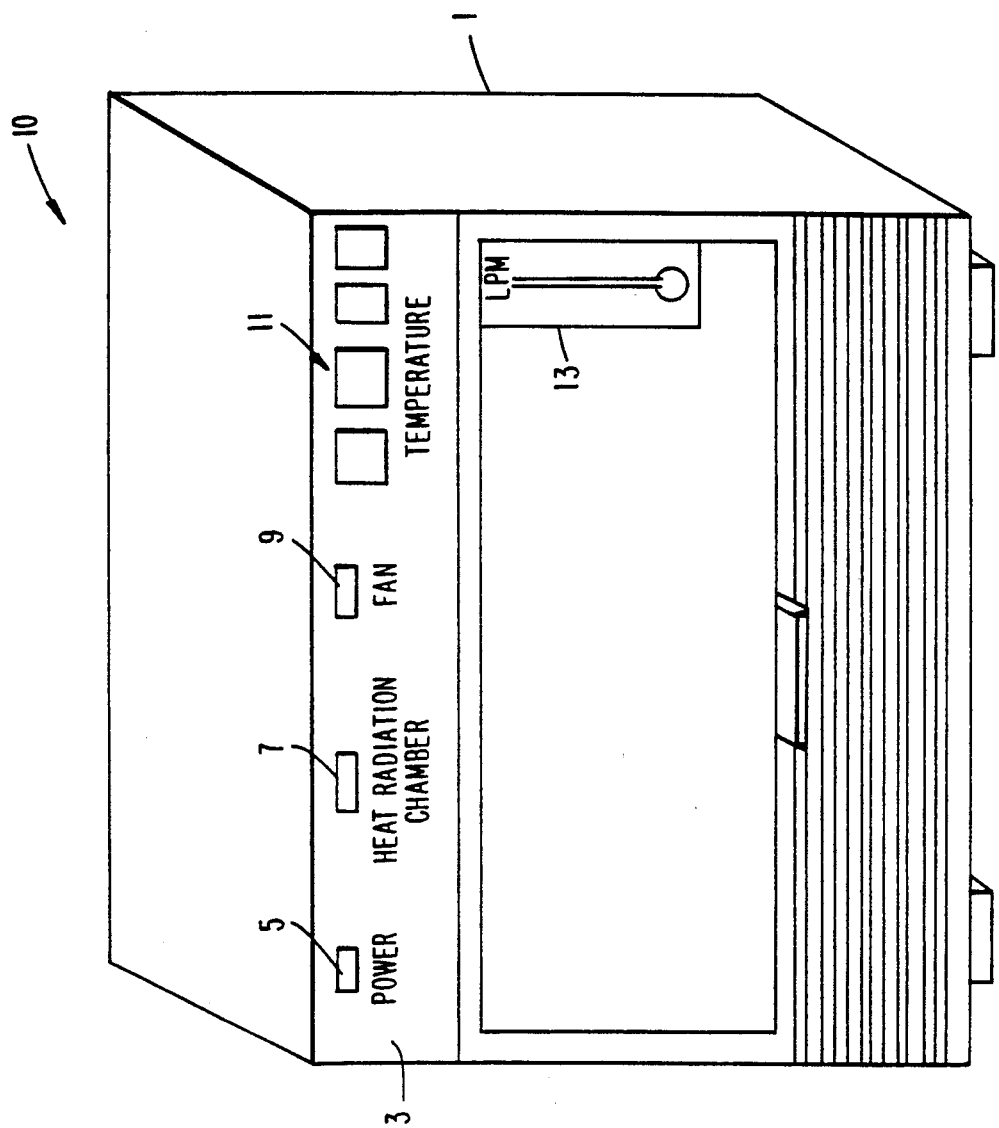
FIG. 7 shows a front perspective view of the apparatus of the present invention.

With reference to FIG. 7, an apparatus for treating air is generally designated by the reference numeral 10 and is seen to include a housing 1 having a control panel 3 thereon. The control panel includes a power indicator 5, an indicator 7 to indicate that the radiation chamber is being heated, an indicator 9 to signal operation of the fan and temperature indicator 11 to relay temperature in the heat radiation chamber. Also included is a flow meter 13 showing a flow rate in liters per minute.

Figure 8:
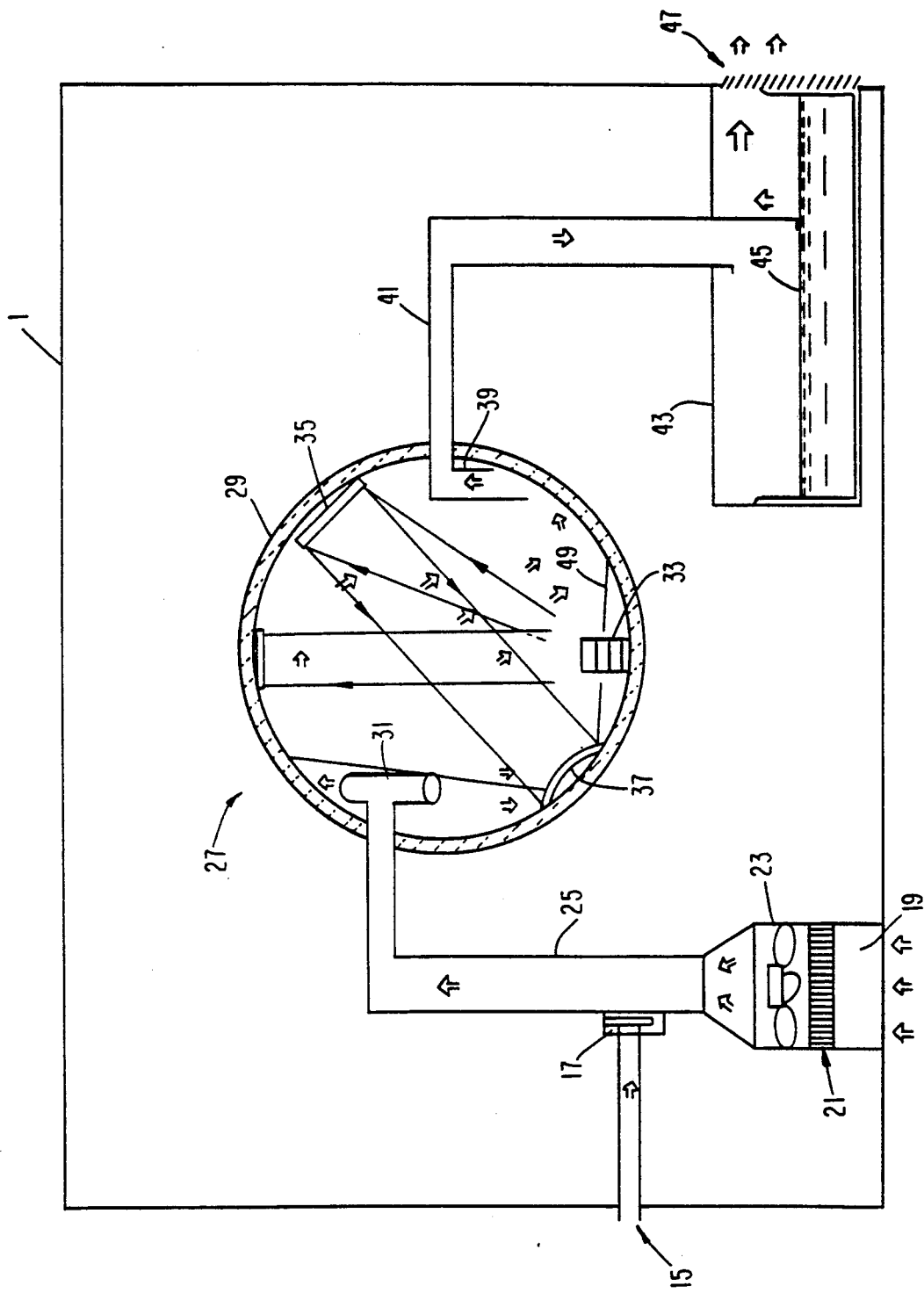
FIG. 8 shows a schematic diagram of the apparatus of the present invention with parts in cross-section to show greater detail.

FIG. 8 shows a schematic view, which is partly in cross-section, identifying the various components of the apparatus of the present invention. The housing 1 includes an outlet 15 and a valve 17 to control flow of atmospheric air through the apparatus. A primary inlet 19 is provided on the bottom of the housing 1. Associated with the inlet 19 is a wool filter 21 and a fan 23. The fan 23 supplies the motive force to pass atmospheric air through the apparatus. The outlet 15 and valve 17 provides a bypass for air entering the inlet 19 so as to control air flow through the apparatus. The valve 17 may be controlled manually or automatically using conventional means.

A duct 25 is provided connecting the inlet 19 to the infrared radiation chamber 27. The infrared radiation chamber 27 includes a sphere 29 configured in the form of a Rowland circle. The sphere is configured in the shape of a Rowland circle to produce the necessary wavelength and frequency, e.g. about 2300-2400 $cm^{-1}$, to activate any carbon dioxide passing through the chamber 27. Use of Rowland circles to achieve a desired wavelength range are well known in the prior art. Accordingly, further description of the manner in which Rowland circles function is not included herein.

The duct 25 entering the chamber 29 has a bifurcated outlet 21 to achieve maximum distribution of the gas passing through the chamber 29. The chamber 29 includes an infrared radiation source such as a 250 watt heat lamp 33. The infrared radiation lamp 33 produces a wavelength of about 1.3 micrometers. The chamber 29 also includes a fixed concave or diffraction grating arranged with respect to the sphere 29 to have Rowland circle characteristics and correct the infrared radiation to the desired 2300-2400 $cm^{-1}$ frequency. A second concave lens 37 is provided to further scatter the corrected wavelength emanating from the concave grating 35. The sphere 29 may also be made of a material capable of birefringence such as pervoskite. The birefringent material minimizes the scattering of the corrected wavelength.

The outlet 39 of the chamber 29 connects to a duct 41 which enters a water chamber 43. The water chamber 43 includes a level of water 45 such that air passing through the chamber 29 must flow through the water prior to exiting the housing at reference numeral 47. The water chamber 43 serves as a filter for removing additional impurities in the atmospheric air passing through the apparatus.

The bifurcated inlet 31 and outlet 39 are configured to maximize the retention time of air in the chamber 29.

In a further embodiment, a 250 watt nichrome wire 49 may be provided in the chamber 29 to further purify air passing through the chamber. The nichrome wire 49 is resistively heated by a power source (not shown) to oxide impurities in the chamber to provide a further treatment of atmospheric air passing through the apparatus. The temperature range of the nichrome wire heat source should be about 600°-700° K. Using the nichrome wire, impurities containing carbon, nitrogen and sulfur can react with oxygen and water in the atmosphere passing through the chamber to form less harmful components.

It should be understood that the size of the inventive apparatus, capacity of the fan and size of the chamber 29 may be determined according to the volume of the space which will be subjected to the inventive air treatment. For example, a plurality of infrared radiation chambers may be used either in series or parallel to increase the volume of treated air. Moreover, the size of the inlet 19 may also be adjusted according to the volume of the area to be treated.

A typical specification for the air treating apparatus of the present invention is set forth below:

| Use area | 60 m³ |
|---|---|
| H × L × W | 50 × 40 × 30 cms |
| filter | multi-glass wool met |
| water tank | 5 L |
| power | 220 V 60 Hz 300 W |
| noise | 40 dB below |
| flow | 1.9 m³/min |
| chamber diameter | 25 cms |

Any known control circuitry may be used in conjunction with the components of the apparatus. As shown in the control panel in FIG. 1 the control circuitry and devices should permit monitoring of process equipment and variables such as temperature, flow rates, fan and infrared radiation source operation, etc.

In using the inventive apparatus, atmospheric air in a given locale such as an office may be treated by passing the atmospheric air continuously through the inventive apparatus to produce an air product containing activated carbon dioxide. Moreover, the treated air will be devoid of minute particles as a result of the filtering action of the inlet filter and outlet filter. When utilizing the embodiment employing a heating means to oxide impurities in the gas, further reductions in harmful components in the atmospheric air will be achieved.

As such, the method and apparatus for treating air of the present invention may be used to cure the lethargic stage created by air conditioners. The inventive apparatus provides increased levels of energy for the carbon dioxide in atmospheric air which may be absorbed by humans in the locale where the air is being treated.

As such, an invention has been disclosed in terms of a preferred embodiment thereof which fulfills each and every one of the objects of the present invention as set forth hereinabove and provides a new and improved apparatus for and method of treating atmospheric air.

Of course, various changes, modifications and alterations from the teachings of the present invention may be contemplated by those skilled in the art without departing from the intended spirit and scope thereof. Accordingly, it is intended that the present invention only be limited by the terms of the appended claims.

I claim:

1. An apparatus for treating air containing carbon dioxide in a predetermined energy state comprising:
   a) a chamber having an inlet, an outlet and inner surface;
   b) an infrared radiation source means arranged on said inner surface for emitting infrared radiation at a predetermined frequency;
   c) a diffraction grating means for receiving and correcting said predetermined frequency to a frequency range between 2300 to 2400 $cm^{-1}$, said grating means disposed on said inner surface;
   d) means for passing atmospheric air into said chamber wherein carbon dioxide molecules in said atmosphere are activated by absorption of said infrared radiation such that said predetermined energy state of carbon dioxide molecules increases; and
   e) means for conducting said air containing carbon dioxide in said increased energy state to atmosphere.

2. The apparatus of claim 1 further comprising a first filtering means for filtering atmospheric air prior to entry into said chamber.

3. The apparatus of claim 1 wherein said means for passing atmospheric air into said chamber further comprises a fan.

4. The apparatus of claim 1 further comprising a second filter means for filtering atmospheric air exiting said outlet of said chamber.

5. The apparatus of claim 4 wherein said second filtering means further comprises a water tank.

6. The apparatus of claim 1 further comprising a heating means disposed within said chamber for oxidizing impurities contained in said atmospheric air.

7. The apparatus of claim 1 wherein said chamber is made of material having birefringent properties.

8. The apparatus of claim 7 wherein said material is pervoskite.

9. The apparatus of claim 1 further comprising a housing enclosing said chamber and said means for passing atmospheric air through said chamber.

10. The apparatus of claim 1 wherein said inlet of said chamber is bifurcated.

11. A method of treating air comprising the steps of:
 a) obtaining a continuous source of air containing carbon dioxide having a predetermined energy state and impurities from the atmosphere;
 b) providing a source of infrared radiation having a frequency between about 2300 and 2400 $cm^{-1}$;
 c) subjecting said air containing impurities and carbon dioxide to said infrared radiation such that said predetermined energy state of carbon dioxide increases; and
 d) conducting said air containing said carbon dioxide in said increased energy state to the atmosphere.

12. The method of claim 11 further comprising the step of filtering said continuous source of air prior to said subjecting step.

13. The method of claim 11 further comprising the step of filtering said air containing carbon dioxide in said increased energy state prior to step (d).

14. The method of claim 11 further comprising the steps of providing a source of heat and subjecting impurities in said air to said source of heat to oxidize said impurities and purify said air.

15. The method of claim 11 wherein said step of providing a source of infrared radiation further comprises providing a source of infrared radiation at a predetermined frequency and correcting said predetermined frequency to about 2300–2400 $cm^{-1}$ using a diffraction grating means.

16. The method of claim 11 wherein said subjecting step is performed at a temperature between about 600° K. and 700° K.

* * * * *